United States Patent [19]

Molloy et al.

[11] Patent Number: 4,626,549

[45] Date of Patent: Dec. 2, 1986

[54] TREATMENT OF OBESITY WITH ARYLOXYPHENYLPROPYLAMINES

[75] Inventors: Bryan B. Molloy, North Salem; Klaus K. Schmiegel, Indianapolis, both of Ind.

[73] Assignee: Eli Lilly and Company, Indianapolis, Ind.

[21] Appl. No.: 846,448

[22] Filed: Mar. 31, 1986

Related U.S. Application Data

[60] Continuation-in-part of Ser. No. 544,654, Oct. 24, 1983, Pat. No. 4,584,404, which is a continuation of Ser. No. 872,147, Jan. 25, 1978, abandoned, which is a division of Ser. No. 432,379, Jan. 10, 1974, Pat. No. 4,314,081.

[51] Int. Cl.$^4$ ............................................. A61K 31/135
[52] U.S. Cl. ..................................... 514/651; 564/347
[58] Field of Search ..................... 514/651, 584, 585

[56] References Cited

U.S. PATENT DOCUMENTS

| | | | |
|---|---|---|---|
| 2,683,742 | 7/1954 | Cusic | 260/570.7 X |
| 3,106,564 | 10/1963 | Fleming et al. | 260/559 B X |
| 3,132,179 | 5/1964 | Clarke | 260/570.6 |
| 3,253,040 | 5/1966 | Potter et al. | 260/570.7 X |
| 3,562,330 | 3/1971 | Nordin | 564/355 |
| 4,018,895 | 4/1977 | Molloy et al. | 424/330 |
| 4,194,009 | 3/1980 | Molloy et al. | 242/330 |
| 4,313,896 | 2/1982 | Molloy et al. | 260/501.18 |
| 4,314,081 | 2/1982 | Molloy et al. | 564/347 |

OTHER PUBLICATIONS

Yoshika et al., "Pharm. Soc. of Japan", vol. 93, pp. 508-528 (1973).

*Primary Examiner*—Robert V. Hines
*Attorney, Agent, or Firm*—Charles W. Ashbrook

[57] ABSTRACT

3-Aryloxy-3-phenylpropylamines and acid addition salts thereof are useful in blocking uptake of monoamines by brain neurons, and are thus effective in treating disorders of sleep, sexual performance, appetite, muscular function, and pituitary function.

9 Claims, No Drawings

TREATMENT OF OBESITY WITH ARYLOXYPHENYLPROPYLAMINES

CROSS-REFERENCE

This is a continuation-in-part of Ser. No. 544,654, filed Oct. 24, 1983, now U.S. Pat. No. 4,584,404, which is a CIP of Ser. No. 872,147 filed Jan. 25, 1978, abandoned, which was a division of Ser. No. 432,379 filed Jan. 10, 1974, now U.S. Pat. No. 4,314,081.

BACKGROUND OF THE INVENTION

Tertiary 2-phenoxy-2-phenylethylamines constitute the subject matter of U.S. Pat. No. 3,106,564. The compounds are said to be useful pharmacological agents exhibiting activity on the central nervous system including useful application as analeptic agents without significant effect on respiration. The compounds are also said to have a high order of activity as antihistaminic and anticholinergic agents. Several tertiary 3-phenoxy-3-phenylpropylamines and quaternary ammonium compounds are disclosed in *J. Pharmaceutical Society*, Japan, 93, 508–519, 1144–53, 1154–61 (1973). The compounds are said to be mydriatic agents.

Secondary and primary 3-aryloxy-3-phenylpropylamines have not hitherto been known.

SUMMARY OF THE INVENTION

This invention provides 3-aryloxy-3-phenylpropylamines of the formula:

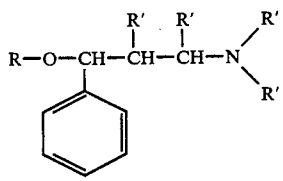

wherein each R' is independently hydrogen or methyl; wherein R is naphthyl or

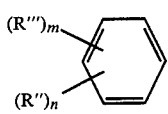

wherein R" and R'" are halo, trifluoromethyl, $C_1$–$C_4$ alkyl, $C_1$–$C_3$ alkoxy or $C_3$–$C_4$ alkenyl; and wherein n and m are 0, 1 or 2; and acid addition salts thereof formed with pharmaceutically-acceptable acids.

In the above formula when R is naphthyl, it can be either α-naphthyl of β-naphthyl. R" and R'" when they are halo, $C_1$–$C_4$ alkyl, $C_1$–$C_3$ alkyloxy or $C_3$–$C_4$ alkenyl represent, illustratively, the following atoms or groups: fluoro, chloro, bromo, iodo, methyl, ethyl, isopropyl, n-propyl, n-butyl, isobutyl, sec.-butyl, t-butyl, methoxy, ethoxy, n-propoxy, isopropoxy, allyl, methallyl, crotyl and the like. R thus can represent o, m and p-trifluoromethylphenyl, o, m and p-chlorophenyl, o, m and p-bromophenyl, o, m and p-fluorophenyl, o, m an p-tolyl, xylyl including all position isomers, o, m and p-anisyl, o, m and p-allylphenyl, o, m and p-methylallylphenyl, o, m and p-phenetolyl(ethoxyphenyl), 2,4-dichlorophenyl, 3,5-difluorophenyl, 2-methoxy-4-chlorophenyl, 2-methyl-4-chlorophenyl, 2-ethyl-4-bromophenyl, 2,4,6-trimethylphenyl, 2-fluoro-4-trifluoromethylphenyl, 2,4,6-trichlorophenyl, 2,4,5-trichlorophenyl, and the like. Compounds illustrative of the scope of this invention include the following:

3-(p-isopropoxyphenoxy)-3-phenylpropylamine methanesulfonate

N,N-dimethyl 3-(3',4'-dimethoxyphenoxy)-3-phenylpropylamine p-hydroxybenzoate

N,N-dimethyl 3-(α-naphthoxy)-3-phenylpropylamine bromide

N,N-dimethyl 3-(β-naphthoxy)-3-phenyl-1-methylpropylamine iodide 3-(2'-methyl-4',5'-dichlorophenoxy)-3-phenylpropylamine nitrate 3-(p-t-butylphenoxy)-3-phenylpropylamine glutarate N-methyl 3-(2'-chloro-p-tolyloxy)-3-phenyl-1-methylpropylamine lactate 3-(2',4'-dichlorophenoxy)-3-phenyl-2-methylpropylamine citrate N,N-dimethyl 3-(m-anisyloxy)-3-phenyl-1-methylpropylamine maleate N-methyl 3-(p-tolyloxy)-3-phenylpropylamine sulfate N,N-dimethyl 3-(2',4'-difluorophenoxy)-3-phenylpropylamine 2,4-dinitrobenzoate 3-(o-ethylphenoxy)-3-phenylpropylamine dihydrogen phosphate N-methyl 3-(2'-chloro-4'-isopropylphenoxy)-3-phenyl-2-methylpropylamine maleate N,N-dimethyl 3-(2'-alkyl-4'-fluorophenoxy)-3-phenylpropylamine succinate N,N-dimethyl 3-(o-isopropoxyphenoxy)-3-phenylpropylamine phenylacetate N,N-dimethyl 3-(o-bromophenoxy)-3-phenyl-propylamine β-phenylpropionate N-methyl 3-(p-iodophenoxy)-3-phenyl-propylamine propiolate N-methyl 3-(3-n-propylphenoxy)-3-phenyl-propylamine decanoate Also included within the scope of this invention are the pharmaceutically-acceptable salts of the amine bases represented by the above formula formed with non-toxic acids. These acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylates, phenyl-substituted alkanoates, hydroxy alkanoates and alkanedioates, aromatic acids, aliphatic and aromatic sulfonic acids etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonates, naphthalene-1-sulfonate, naphthalene-2-sulfonate, mandelate and the like salts.

The compounds of this invention in the form of their free bases are high boiling oils, but white crystalline solids in the form of their acid addition salts. The compounds can be prepared in several ways. A particularly useful procedure for preparing compounds represented by the above formula (in which both R' groups attached to the nitrogen are methyl) involves the reduction of β-dimethylaminopropiophenone produced by a Mannich reaction to yield N,N-dimethyl 3-phenyl-3-hydroxy-propylamine. Replacement of the hydroxyl group with a halogen, such as chlorine, yields the corresponding N,N-dimethyl 3-phenyl-3-chloropropylamine. Reaction of this chloro compound with a suitably substituted phenol, as for example o-methoxyphenol (guiacol), produces a compound of this invention in which both R' groups are methyl. Treatment of the N,N-dimethyl compound with cyanogenbromide serves to replace one N-methyl group with a cyano group. Hydrolysis of the resulting compound with base yields a compound of this invention in which only one R' group on the nitrogen is methyl. For example, treatment of N,N-dimethyl 3-(o-anisyloxy)-3-phenylpropylamine with cyanogen bromide followed by alkaline hydrolysis of the N-cyano compound yields directly N-methyl 3-(o-anisyloxy)-3-phenylpropylamine [N-methyl 3-(o-methoxy phenoxy)-3-phenylpropylamine].

An alternate preparation of the compounds of this invention in which only one of the R' groups attached to the nitrogen is methyl is carried as follows:

3-Chloropropylbenzene is reacted with a positive halogenating agent such N-bromosuccinimide to yield the corresponding 3-chloro-1-bromopropylbenzene. Selective replacement of the bromo atom with the sodium salt of a phenol, as for example, the sodium salt of o-methoxyphenol (guiacol) yields a 3-chloro-1-(1-methoxyphenoxy)-propylbenzene [also named as 3-chloro-1-(o-anisyloxy)propylbenzene]. Reaction of the 3-chloro derivative thus produced with methylamine yields the desired N-methyl 3-(o-anisyloxy)-3-phenyl-propylamine.

Compounds in which both R' groups attached to the nitrogen in the above formula are hydrogen can be prepared from an intermediate produced in the previous preparation of the N-methyl compounds such as, for illustrative purposes, 3-chloro-1-(o-anisyloxy)-propylbenzene prepared by the reaction of 3-chloro-1-bromobenzene and sodium guiacol. This chloro compound is reacted with sodium azide to give the corresponding 3-azido-1-(o-anisyloxy)-propylbenzene. Reduction of the azide group with a metallo-organic reducing agent such as sodium borohydride yields the desired primary amine. Alternatively, the chloro compound can be reacted directly with a large excess of ammonia in a high pressure reactor to give the primary amine.

Compounds in which the R' group on the carbon atom alpha to the nitrogen is methyl can be prepared by reacting phenyl 2'-propenyl ketone with dimethylamine [See *J. Am. Chem. Soc.*, 75, 4460 (1953)]. The resulting 3-dimethylaminobutyrophenone is reduced to yield the N,N-dimethyl 3-hydroxy-1-methyl-3-phenylpropylamine. Replacement of the hydroxyl with chlorine followed by reaction of the chloro-compound with the sodium salt of a suitably substituted phenol yields the N,N-dimethyl derivatives of this invention bearing an alpha methyl group on the propylamine backbone of the molecule. Production of the corresponding N-methyl derivative can be accomplished by the aforementioned reaction sequence utilizing cyanogen bromide. The N-methyl derivative can in turn be converted to the corresponding primary amine (in which both R' groups on the nitrogen are hydrogen) by oxidation in neutral permanganate according to the procedure of Booher and Pohland, Ser. No. 317,969, filed Dec. 26, 1972. Compounds in which the R' group attached to the β-carbon atom is methyl are prepared by a Mannich reaction involving propiophenone, formaldehyde and dimethylamine. The resulting ketone, a α-methyl-β-dimethylaminopropiophenone, is subjected to the same reduction procedure as before to yield a hydroxy compound. Replacement of the hydroxyl with chlorine followed by reaction of the chloro compound with the sodium salt of a phenol yields a dimethyl amine compound of this invention. Conversion of the dimethylamine to the corresponding monomethyl and primary amines is carried out as before.

Those compounds in which the R' group attached to either the α or β-carbon is methyl have two asymmetric carbon atoms, the carbon carrying the R' methyl and the γ-carbon carrying the phenoxy and phenyl groups. Thus, such compounds exist in four diastereomeric forms occurring as two racemic pairs, the less soluble pair being designated α-dl form and the more soluble the β-dl form. Each racemate can be resolved into its individual d and l isomers by methods well known in the art, particularly, by forming salts with optically active acids and separating the salts by crystallization.

This invention is further illustrated by the following specific examples:

EXAMPLE 1

Preparation of N-methyl 3-(p-trifluoromethylphenoxy)-3-phenylpropylamine and of N,N-dimethyl 3-(p-trifluoromethylphenoxy)-3-phenylpropylamine About 600 g. of β-dimethylaminopropiophenone hydrochloride were converted to the corresponding free base by the action of 1.5N aqueous sodium hydroxide. The liberated free base was taken up in ether, the ether layer separated and dried, and the ether removed therefrom in vacuo. The residual oil comprising β-dimethylaminopropiophenone was dissolved in two liters of tetrahydrofuran, and the resulting solution added in dropwise fashion with stirring to a solution of four moles of diborane in four liters of tetrahydrofuran. The reaction mixture was stirred overnight at room temperature. An additional mole of diborane in one liter of tetrahydrofuran was added, and the reaction mixture stirred again overnight at room temperature. Next, two liters of aqueous hydrochloric acid were added to decompose any excess diborane present. The tetrahydrofuran was removed by evaporation. The acidic solution was extracted twice with one liter portions of benzene, and the benzene extracts were discarded. The acidic solution was then made basic with an excess of 5N aqueous sodium hydroxide. The basic solution was extracted three times with two liter portions of benzene. The benzene extracts were separated and combined, and the combined extracts washed with a saturated aqueous sodium chloride and then dried. Evaporation of the solvent in vacuo yields 442 g. of N,N-dimethyl 3-phenyl-3-hydroxypropylamine.

A solution containing 442 g. of N,N-dimethyl 3-phenyl-3-hydroxypropylamine in 5 l. of chloroform was saturated with dry gaseous hydrogen chloride. 400 ml. of thionyl chloride were then added to the chloroform solution at a rate sufficient to maintain reflux. The solution was refluxed an additional 5 hours. Evaporation of the chloroform andd other volatile constituents in vacuo yielded N,N-dimethyl 3-phenyl-3-chloropropylamine hydrochloride which was collected by filtration, and the filter cake washed twice with 1500 ml. portions of acetone. The washed crystals weighed about 500 g. and melted at 181°–3° C. with decomposition. An additional 30 g. of compound were obtained from the acetone wash by standard crystallization procedures. The structure of the above compound was verified by NMR and titration.

A solution of 50 g. p-trifluoromethylphenol, 12 g. of solid sodium hydroxide and 400 ml. of methanol was placed in a one liter round-bottom flask equipped with magnetic stirrer, condenser and drying tube. The reaction mixture was stirred until the sodium hydroxide had dissolved. Next, 29.8 g. of N,N-dimethyl 3-phenyl-3-chloropropylamine hydrochloride were added. The resulting reaction mixture was refluxed for about 5 days and then cooled. The methanol was then removed by evaporation, and the resulting residue taken up in a mixture of ether and 5N aqueous sodium hydroxide. The ether layer was separated and washed twice with 5N aqueous sodium hydroxide and three times with water. The ether layer was dried, and the ether removed by evaporation in vacuo to yield as a residue N,N-dimethyl 3-(p-trifluoromethylphenoxy)-3-phenylpropylamine.

The free base was converted to the corresponding oxalate salt by dissolving 32 g. of the amine in ethyl acetate to which was added a solution of 9 g. of oxalic acid also in ethyl acetate. N,N-dimethyl-3-p-trifluoromethylphenoxy-3-phenylpropylamine oxalate thus formed melted at 117°–119° C. with decomposition after recrystallization from ethyl acetate.

Analysis calc.: C, 58.11; H, 3.36; N, 3.39; F, 13.79; Found: C, 58.19; H, 3.49; N, 3.59; F, 13.85.

A solution containing 8.1 g. of cyanogen bromide in 500 ml. benzene and 50 ml. of toluene was placed in a one liter three-neck round-bottom flask equipped with thermometer, addition funnel, drying tube and inlet tube for nitrogen. The solution was cooled to about 5° C. with stirring, and nitrogen gas was bubbled thru the solution. Next, a solution of 12.146 g. of N,N-dimethyl 3-(p-trifluoromethylphenoxy)-3-phenylpropylamine dissolved 40 ml. of benzene was added in dropwise fashion. The temperature of the reaction mixture was allowed to rise slowly to room temperature, at which temperature stirring was continued overnight while still maintaining a nitrogen atmosphere. 100 ml. of benzene were added. The reaction mixture was washed twice with water, once with 2N aqueous sulfuric acid and then with water until neutral. The organic layer was dried, and the solvents removed therefrom by evaporation in vacuo to yield about 9.5 g. of an oil comprising N-methyl-N-cyano 3-(p-trifluoromethylphenoxy)-3-phenylpropylamine.

A solution of 100 g. potassium hydroxide, 85 ml. water, 400 ml. ethylene glycol and 9.50 g. of N-methyl-N-cyano 3-(p-trifluoromethylphenoxy)-3-propylamine was prepared in a one liter three-neck, round-bottom flask equipped with magnetic stirrer and condenser. The reaction mixture was heated to refluxing temperature (130° C.) for 20 hours, and was then cooled. 500 ml. of water were added. The reaction mixture was extracted with three 500 ml. portions of ether. The ether extracts were combined, and the combined extracts washed with water. The water wash was discarded. The ether solution was next contacted with 2N aqueous hydrochloric acid. The acidic aqueous layer was separated. A second aqueous acidic extract with 2N hydrochloric acid was made followed by three aqueous extracts and an extract with saturated aqueous sodium chloride. The aqueous layers were all combined and made basic with 5N aqueous sodium hydroxide. N-methyl 3-(p-trifluoromethylphenoxy)-3-phenylpropylamine, formed in the above reaction, was insoluble in the basic solution and separated. The amine was extracted into ether. Two further ether extractions were carried out. The ether extracts were combined, and the combined extracts washed with saturated aqueous sodium chloride and then dried. Evaporation of the ether in vacuo yielded about 6.3 g. of N-methyl 3-(p-trifluoromethylphenoxy)-3-phenylpropylamine. The amine free base was converted to the corresponding oxalate sale by the method set forth above. N-methyl 3-(p-trifluoromethylphenoxy)-3-phenylpropylamine oxalate thus prepared melted at 179°–182° C. with decomposition after recrystallization from an ethyl acetate-methanol solvent mixture. Analysis calc.: C, 57.14; H, 5.05; N, 3.51; F, 14.27; Found; C, 57.43; H, 5.30; N, 3.79; F, 14.24.

The amine free base was also converted to the maleate salt.

The following N,N-dimethyl or N-methyl 3-substituted phenoxy-3-phenylpropylamines were prepared by the above procedures.

N,N-dimethyl 3-(o-chlorophenoxy)-3-phenylpropylamine maleate which melted at 88°–90° C. after recrystallization from an ethyl acetate-cyclohexane solvent mixture. Analysis calc.: C, 62.14; H, 5.96; N, 3.45; Cl, 8.73; Found; C, 61.94; H, 5.67; N, 3.68; Cl, 8.92.

N,N-dimethyl 3-(o-trifluoromethylphenoxy)-3-phenylpropylamine p-toluene-sulfonate which melted at 134°–6° C. after recrystallization from ethyl acetate. Analysis calc.; C, 60.59; H, 5.70; N, 2.83; F, 11.50; S, 6.47; Found; C, 60.36, H, 5.52; N, 3.12; F, 11.80; S, 6.66.

N,N-dimethyl 3-(o-tolyloxy)-3-phenylpropylamine oxalate which melted at 160°–62° C. after recrystallization from a methanol-isopropanol solvent mixture. Analysis calc.: C, 66.84; H, 7.01; N, 3.90; Found; C, 66.82; H, 7.07; N, 4.17.

N,N-dimethyl 3-(β-naphthyloxy)-3-phenylpropylamine oxalate: melting point=145°–7° C. Analysis calcd.: C, 69.86; H, 6.37; N, 3.54; Found: C, 69.80; H, 6.50; N, 3.74.

N-methyl 3-phenyl-3-(m-chlorophenoxy)propylamine oxalate: melting point=177°–9° C. Analysis calc.; C, 59.10; H, 5.51; N, 3.83; Cl, 9.69; Found; C, 58.89; H, 5.45; N, 4,07; Cl, 9.24.

N,N-dimethyl 3-phenyl-3-(m-methoxyphenoxy)-propylamine oxalate: melting point=125°–8° C. Analysis calc.: C, 63.99; H, 6.91, N, 3.73; Found: C, 63.93; H, 6.90; N, 3.59.

N,N-dimethyl 3-phenyl-3-(o-allylphenoxy)propylamine oxalate: melting point=159°–161° C. Analysis calc.: C, 68.55; H, 7.06; N, 3.63; Found; C, 68.67; H, 7.15; N, 3.83.

N,N-dimethyl 3-phenyl-3-(p-chlorophenoxy)-propylamine oxalate: melting point=139°–141° C. Analysis calc.: C, 60.08; H, 5.84; N, 3.69; Cl, 9.33; Found; C, 60.34, H, 5.95; N, 3.88; Cl, 9.61.

N,N-dimethyl 3-(o-methoxyphenoxy)-3-phenylpropylamine maleate: m.p.=98°–103° C. Analysis calc.: C, 65.82; H, 6.78; N, 3.49; Found; C, 65.83; H, 6.52; N, 3.63.

N,N-dimethyl 3-(p-methoxyphenoxy)-3-phenylpropylamine maleate: m.p.=101°–104° C. Analysis calc.: C, 65.82; H, 6.78; N, 3.49; Found; C, 65.96; H, 6.50; N, 3.68.

N-methyl 3-(p-fluorophenoxy)-3-phenylpropylamine maleate: m.p.=112.5°-119° C. Analysis calc.: C, 63.99; H, 5.91; N, 3.73; Found; C, 63.77; H, 6.19; N, 3.90.

N-methyl 3-(p-methoxyphenoxy)-3-phenylpropylamine maleate: m.p.=128.5°-135° C. Analysis calc.: C, 65.10; H, 6.50; N, 3.62; Found; C, 64.94; H, 6.54; N, 3.67.

N,N-dimethyl 3-(o-bromophenoxy)-3-phenylpropylamine oxalate: melting point=144°-6° C. Analysis calc; C, 53.79 H, 5.23; N, 3.30; Br, 18.86; Found, C, 53.84; H, 5.52; N, 3.38; Br, 18.86.

N,N-dimethyl 3-(p-tolyloxy)-3-phenylpropylamine oxalate: melting point=145°-147° C. Analysis calc.; C, 66.84; H, 7.01; N, 3.90: Found; C, 66.61; H, 7.01; N, 4.06.

N-methyl 3-phenyl-3-(o-allylphenoxy)propylamine oxalate: melting point=144°-147° C. (dec.). Analysis calc.: C, 67.91; H, 6.78; N, 3.77; Found; C, 67.90; H, 6.85; N, 3.96.

N-methyl 3-phenyl-3-(p-tolyloxy)propylamine oxalate: melting point=170°-173° C. Analysis calc.; C, 66.07; H, 6.71, N, 4.06; Found; C, 65.93; H, 6.57; N, 3.87.

N,N-dimethyl 3-phenyl-3-(m-tolyloxy)propylamine oxalate: melting point=134°-6° C. Analysis calc.; C, 66.83; H, 7.01; N, 3.90; Found; C, 66.48; H, 7.32; N, 4.32.

N,N-dimethyl 3-phenyl-3-(m-trifluoromethylphenoxy)propylamine oxalate: melting point=163°-5° C. Analysis calc.; C, 58.11; H, 5.36; N, 3.39; F, 13.79; Found; C, 57.89; H, 5.26; N, 3.41; F, 13.69.

N,N-dimethyl 3-phenyl-3-(o-t-butylphenoxy)propylamine oxalate: melting point=146°-9° C. Analysis calc.; C, 68.88; H, 7.78; N, 3.49; Found; C, 68.56; H, 8.04; N, 3.69

N-methyl 3-phenyl-3-(p-fluorophenoxy)propylamine oxalate: melting point=159°-161° C. Analysis calc.; C, 61.88; H, 5.77; N, 4.01; F, 5.44; Found; C, 61.66; H, 5.90; N, 3.72, F, 5.70.

N-methyl 3-phenyl-3-(o-methoxyphenoxy)propylamine hydrochloride: melting point=105°-8° C. (recrystallized from ethyl acetate); Analysis calc.; C, 66.33, H, 7.20, N, 4.55, Cl, 11.52; Found; C, 66.16; H, 7.36; N, 4.41; Cl, 11.48.

N-methyl 3-phenyl-3-(o-fluorophenoxy)propylamine oxalate, melting point=148°-50° C. Analysis calc.: C, 61.88; H, 5.77; N, 4.01; F, 5.44; Found; C, 61.83; H, 5.97; N, 4.14; F, 5.65.

N-methyl 3-phenyl-3-(m-methoxyphenoxy)propylamine oxalate; melting point=140°-3° C. Analysis calc.: C, 63.15; H, 6.42; N, 3.88; Found; C, 62.91; H, 6.40; N, 4.17.

N-methyl 3-phenyl-3-(o-tolyloxy)propylamine oxalate: melting point=155°-7° C. Analysis calc.: C, 66.07; H, 6.71; N, 4.06; Found; C, 65.81; H, 6.94; N, 4.36.

N,N-dimethyl 3-(o-ethylphenoxy)-3-phenylpropylamine oxalate: melting point=152°-4° C. Analysis calc.: C, 67.54; H, 7.29, N, 3.75; Found; C, 67.33; H, 7.05, N, 3.98.

N,N-dimethyl 3-(o-isopropoxyphenoxy)-3-phenylpropylamine oxalate: melting point=139°-142° C. Analysis calc.; C, 68.20; H, 7.54; N, 3.61; Found, C, 68.50; H, 7.82, N, 3.85.

N-methyl 3-phenyl-(p-chlorophenoxy)propylamine oxalate: melting point=163°-5° C. Analysis calc.; C, 59.10; H, 5.51; N, 3.83; Cl, 9.69; Found; C, 59.33; H, 5.58; N, 4.07; Cl, 9.45.

N,N-dimethyl 3-(p-fluorophenoxy)-3-phenylpropylamine maleate: melting point=103°-8° C. Analysis calc.: C, 64.77; H, 6.21; N, 3.60; Found: C, 64.79; H, 6.50; N, 3.82.

N,N-dimethyl 3-(m-chlorophenoxy)-3-phenylpropylamine oxalate: melting point=150°-2° C. (recrystallization from isopropanol) Analysis calc.: C, 60.08; H, 5.87; N, 3.69; Cl, 9.33; Found: C, 59.90; H, 6.08; N, 3.42; Cl, 9.60.

N,N-dimethyl 3-(o-fluorophenoxy)-3-phenylpropylamine hydrochloride: melting point=166°-8° C. (from acetone-cyclohexane) Analysis calc.: C, 65.91; H, 6.83; N, 4.52; Cl, 11.99; F, 6.13; Found: C, 65.78; H, 6.82; N, 4.78; Cl, 11.70; F, 5.99.

N-methyl 3-phenoxy-3-phenyl-2-methylpropylamine oxalate: melting point=158°-160° C. (from isopropanol) Analysis calc.: C, 66.07; H, 6.71; N, 4.06; Found: C, 66.12; H, 6.72; N, 4.26

N-methyl 3-phenoxy-3-phenyl-1-methylpropylamine oxalate: melting point=80°-100° C. with decomposition (from ethyl acetate) Analysis calc.: C, 66.07; H, 6.71; N, 4.06; Found: C, 65.85; H, 6.45, N, 4.20.

α-Dl-N,N-dimethyl-3-phenoxy-3-phenyl-1-methylpropylamine oxalate: melting point=113°-16° C. Analysis calc.: C, 66.84; H, 7.01; N, 3.90; Found: C, 67.03; H, 7.20; N, 4.13.

N,N-dimethyl 3-phenoxy-3-phenyl-2-methylpropylamine oxalate: melting point=130°-4° C. Analysis calc.: C, 66.89; H, 7.01; N, 3.90; Found: C, 66.59; H, 7.08; N, 3.96.

N-methyl 3-(m-fluorophenoxy)-3-phenylpropylamine oxalate: melting point=177°-9° C. Analysis calc.: C, 61.87; H, 5.77; N, 4.01; F, 5.44; Found: C, 62.07, H, 6.02, N, 4.23, F, 5.23.

N,N-dimethyl 3-(o-ethoxyphenoxy)-3-phenylpropylamine oxalate: melting point=101°-4° C. Analysis calc.: C, 64.77; H, 6.99, N, 3.60; Found: C, 65.05; H, 7.00; N, 3.88.

N,N-dimethyl 3-(p-fluoro-o-tolyloxy)-3-phenylpropylamine oxalate: melting point=149°-51° C. Analysis calc.: C, 63.65; H, 6.41; N, 3.71; F, 5.03; Found: C, 63.82; H, 6.66; N, 3.95; F, 5.32.

N,N-dimethyl 3-(α-naphthyloxy)-3-phenylpropylamine maleate: melting point=97°-99° C. Analysis calc.: C, 70.48; H, 6.65; N, 3.42; Found: C, 69.80; H, 6.50; N, 3.74.

β-dl-N,N-dimethyl-3-phenoxy-3-phenyl-1-methylpropylamine oxalate: melting point=131°-33° C. Analysis calc.: C, 66.89; H, 7.01; N, 3.90; Found: C, 66.64; H, 7.00; N, 3.77.

EXAMPLE 2

Preparation of N-methyl 3-(o-methoxyphenoxy)-3-phenylpropylamine hydrochloride.

A reaction mixture consisting of 1000 g. of 3-chloropropylbenzene, 1500 g. of N-bromosuccinimide, 5 g. of benzoyl peroxide and 6 l. of carbon tetrachloride were placed in a 12 l. 3-neck, round-bottom flask equipped with stirrer and condenser. The reaction mixture was stirred and heated until an exothermic reaction began. The heat source was then removed, and the refluxing of reaction mixture controlled by external cooling. After the reaction had been completed as noted by the disappearance of the N-bromosuccinimide, the reaction mixture was cooled and crystalline succinimide collected by filtration. The succinimide filter cake was washed with carbon tetrachloride. The combined filtrate and wash was concentrated in vacuo. The residue comprising 3-chloro-1-bromopropylbenzene obtained in the above reaction was shown by a NMR to be the desired material and was used without further purification. The yield was essentially quantitative.

Next, a solution of sodium guaiacol (o-methoxyphenol) was prepared by dissolving 156 g. of sodium hydroxide and 485.6 g. of guaiacol in 2.5 l. of ethanol. The ethanol was removed by evaporation in vacuo, benzene added, and the benzene also removed by evaporation in vacuo. This process was repeated several times in order to dry completely the sodium guaiacol. The sodium guaiacol obtained by the above procedure was dissolved in approximately 3 l. of dimethylsulfoxide. The solution was cooled to about 20° C. 3-chloro-1-bromopropylbenzene was added thereto in dropwise fashion over a period of ¾ hour while the reaction temperature was maintained at about 25° C. The reaction mixture was allowed to stir at room temperature overnight and was then poured onto ice. The resulting aqueous layer was extracted with four 2 l. portions of hexane. The hexane extracts were washed with water and dried. Removal of the hexane in vacuo yielded as a residue 3-chloro-1-(o-methoxyphenoxy)propylbenzene prepared by the above procedure. The compound was distilled in vacuo. 3-Chloro-1-(o-methoxyphenoxy)propylbenzene thus purified distilled in the range 135°-145° C. (0.03 torr). The structure of the compound was verified by NMR.

A reaction mixture consisting of 200 ml. of methylamine, 225 ml. of methanol and 75 g. of 3-chloro-1-(o-methoxyphenoxy)propylbenzene was heated in an autoclave for 12 hours at 140° C. The reaction mixture was cooled, and the solvent was removed by evaporation. The semisolid residue was mixed with concentrated aqueous sodium hydroxide. The reasulting mixture was extracted several times with ether. N-methyl 3-(o-methoxyphenoxy)-3-phenylpropylamine, formed in the above reaction, was insoluble in the alkaline solution and was extracted therefrom with ether. The ether extracts were combined, and the combined extracts washed with water and dried. The ether was removed therefrom in vacuo leaving the amine as a dark colored residue. The residue was dissolved in ether and 1 equivalent of oxalic acid in methanol added slowly. N-methyl 3-(o-methoxyphenoxy)-3-phenylpropylamine oxalate formed an insoluble precipitate which was collected by filtration, and the filter cake washed with ether and dried. N-methyl 3-(o-methoxyphenoxy)-3-phenylpropylamine oxalate melted at 150°-152° C. The NMR spectrum of the compound was consistent with the expected structure.

N-methyl 3-(o-methoxyphenoxy)-3-phenylpropylamine oxalate was dissolved in a minimum quantity of water with heating, and concentrated aqueous sodium hydroxide added. After cooling, the alkaline solution was extracted several times with ether. The combined ether extracts were washed with water and dried, and the ether removed therefrom in vacuo. N-methyl 3(o-methoxyphenoxy)-3-phenylpropylamine free base thus isolated was dissolved in ether, and the ether solution saturated with dry gaseous hydrogen chloride. N-methyl 3(o-methoxyphenoxy)-3-phenylpropylamine hydrochloride thus formed was recrystallized from ethyl acetate containing a small amount of methanol. N-methyl 3-(o-methoxyphenoxy)-3-phenylpropylamine hydrochloride thus prepared and purified melted at 129°-131° C.

EXAMPLE 3

Preparation of 3-(o-methoxyphenoxy)-3-phenylpropylamine

A solution of 2.6 g. of sodium azide in 10 ml. of water was placed in a 100 ml. three-neck, round-bottom flask equipped with stirrer, condenser and thermometer. A second solution containing 2.76 g. of 3-chloro-1-(o-methoxyphenoxy)propylbenzene (as provided by the procedure of Example 2) in 30 ml. of dimethylformamide was added to the sodium azide solution, and the resulting mixture heated at 95° C. overnight. The reaction mixture was cooled, diluted with water and extracted three times with ether. The ether extracts were combined, the combined extracts were washed five times with water followed by a saturated aqueous sodium chloride wash, and were then dried. Evaporation of the ether in vacuo yielded a colorless liquid comprising 3-azido-1-(o-methoxyphenoxy)propylbenzene. Forty-one grams of this latter compound were dissolved in 350 ml. of isopropanol. The resulting solution was placed in a 1 l. round-bottom flask equipped with magnetic stirrer condenser and drying tube. Fifteen and two-tenths grams of 96% sodium borohydride in the solid form were added to the azide solution. The resulting mixture was heated to refluxing temperature overnight and then cooled. The alcohol was evaporated therefrom in vacuo. About 1.5 l. of water were added, and the resulting aqueous mixture acidified cautiously with 2N aqueous hydrochloric acid. 3-(o-methoxyphenoxy)-3-phenylpropylamine produced in the above reaction was soluble in the aqueous acidic layer as the hydrochloride salt. The acidic aqueous layer was extracted three times with ether, and the ether extracts saved to recover unreacted starting material. The acidic layer was then made basic with 5N aqueous sodium hydroxide. The primary amine, being insoluble in base, separated and was extracted into ether. The ether layer was separated, and the aqueous alkaline layer extracted twice more with ether. The ether extracts were combined, and the combined layers washed with a saturated aqueous sodium chloride solution. Evaporation of the ether in vacuo yielded about 17 g. of 3-(o-methoxyphenoxy)-3-phenylpropylamine which was converted to the oxalate sale by the procedure of Example 1. 3-(o-methoxyphenoxy)-3-phenylpropylamine oxalate thus prepared melted at 118°-121° C. after recrystallization from an ethyl acetate-cyclohexane solvent mixture. The oxalate salt was converted to the hydrochloride salt by forming the free base in ether solution and then saturating the ether solution with gaseous hydrogen chloride. The hydrochloride salt melted at 77°-8° C. Analysis calc.: C, 65.91; H, 6.86; N, 4.77; Cl, 12.07; Found: C, 65.13; H, 7.12; N, 4.61; Cl, 12.21.

Following the above procedure, 3-(p-trifluoromethylphenoxy)-3-phenylpropylamine oxalate was prepared: melting point=162°-164° C. The oxalate salt was converted to the hydrochloride salt by forming the free base, extracting the free base into ether and then saturating an ether solution of the free base with gaseous hydrogen chloride. The hydrochloride salt melted at 130°-133° C. Analysis calc.: C, 57.93; H, 5.17; N, 4.22; Cl, 10.69; F, 17.18; Found: C, 5.66; H, 5.08; N, 4.09; Cl, 11.15; F, 16.66.

EXAMPLE 4

Preparation of 3-phenoxy-3-phenylpropylamine

Eight grams of 3-phenoxy-3-phenylpropylchloride provided by the procedure of Example 2 were heated with 150 ml. of liquid ammonia in a high pressure reactor at 100° C. for 20 hours. The volatile constituents of the reaction mixture were evaporated, and the residue, comprising 3-phenoxy-3-phenylpropylamine formed in the above reaction, was dissolved in ethanol and the volatile constituents again removed by evaporation. The resulting residue was dissolved in a mixture of ether and 5N aqueous sodium hydroxide. The ether layer was separated, and the alkaline aqueous layer extracted three more times with ether. The ether extracts were combined, and the combined extracts washed with water. The ether layer was next extracted twice with 2N aqueous hydrochloric acid, the primary amine passing into the acidic layer. The acidic extracts were combined and made basic by the addition of an excess of 5N aqueous sodium hydroxide. The primary amine, being insoluble in the basic solution, separated and was extracted into ether. The ether extract was separated, and the basic solution extracted twice more with ether. The ether extracts were combined, the combined extracts washed with saturated aqueous sodium chloride and then dried. Evaporation of the ether in vacuo yielded 3-phenoxy-3-phenylpropylamine as an oil. The oxalate salt of the primary amine was prepared by the procedure of Example 1 and melted at 170°–173° C. Analysis calc.: C, 64.34; H, 6.04; N, 4.41; Found: C, 64.49; H, 5.80; N, 4.67.

EXAMPLE 5

Preparation of Salts

Salts of the free bases of this invention, other than the hydrochloride, maleate and oxalate salts whose preparation is illustrated in Examples 1–4, are prepared by dissolving the free base in ether and adding an equivalent of a suitable non-toxic acid, also in ether. The salts thus formed, as for example the acetate and benzoate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include the sulfate, hydrobromide, phosphate, hydrogen phosphate, dihydrogen phosphate, acetate, methenesulfonate, succinate, tartrate, citrate, benzoate, and p-toluene sulfonate salts.

As indications of their psychotropic activity, the compounds of this invention have been found to block the uptake of various physiologically active monoamines. This blockade is shown both in vitro with radioactive labelled compounds to determine the amount of monoamine uptake by synaptosomes from rat brain, and in vivo by a variety of methods. Among the physiologically active monoamines whose uptake is blocked by the compounds of this invention are included serotonin, norepinephrine and dopamine (3,4-dihydroxyphenylethylamine). While all of the compounds of this invention block the uptake of monoamines, certain of them possess a unique selectivity in that they block the uptake of one of the monoamines to a far greater extent than they do the uptake of the other two. Tables 1 and 2 which follow set forth the results of some of the in vitro determinations of the blockage of monoamine uptake by the compounds of this invention. In the tables, column 1 gives the R substituent on the 3-phenylpropylamine and columns 2–4, the concentration in micrograms per ml. that blocks the uptake of a particular amine by 50 percent for the amines—norephinephrine, serotonin, and dopamine. At the head of each column is given the concentration of the particular monoamine used in the experiment.

TABLE 1

$$R-O-CH(C_6H_5)-CH_2-CH_2-N(CH_3)_2$$

Concentration in mcg./ml. that blocks 50% of amine uptake

| R | Norepinephrine 0.48 μM | Serotonin 0.1 μM | Dopamine 0.2 μM |
|---|---|---|---|
| m-fluorophenyl | .15 | .01 | .6 |
| phenyl | 1 | .6 | .3 |
| α-naphthyl | 3 | .03 | 2.5 |
| p-chlorophenyl | .3 | .03 | 1.3 |
| m-methoxyphenyl | .2 | .08 | .5 |
| m-trifluoromethylphenyl | 8 | .18 | >100 |
| o-bromophenyl | — | .1 | 5 |
| m-chlorophenyl | .02 | .15 | 2 |
| p-trifluoromethylphenyl | 70 | .16 | >100 |
| o-chlorophenyl | .45 | .2 | .2 |
| o-tolyl | .35 | 2 | 0.8 |
| m-tolyl | 12 | .7 | >0 |
| p-tolyl | .015 | .4 | >100 |
| o-ethylphenyl | >100 | 3.5 | >100 |
| o-isopropylphenyl | 1.5 | >100 | >100 |
| o-t-butylphenyl | 1.5 | 40 | >100 |
| o-allylphenyl | 1 | .8 | 50 |
| o-trifluoromethylphenyl | 70 | .16 | >100 |
| o-anisyl | .3 | 2.6 | 20 |
| p-anisyl | 7 | 1 | 3.6 |
| o-phenetyl | 3 | 6 | >100 |
| o-fluorophenyl | .05 | .3 | .35 |
| p-fluorophenyl | >100 | 1 | .45 |
| β-naphthyl | >100 | 1 | >100 |
| 4-fluoro-o-tolyl | 2.5 | .6 | 40 |
| 2,4-difluorophenyl | .2 | .3 | 10 |

TABLE 2

$$R-O-CH(C_6H_5)-CH_2-CH_2-NH-CH_3$$

Concentration in mcg./ml. that blocks 50% of amine uptake

| R | Norepinephrine 0.48 μM | Serotonin 0.1 μM | Dopamine 0.2 μM |
|---|---|---|---|
| p-trifluoromethylphenyl | 20 | .06 | >100 |
| m-chlorophenyl | .07 | .15 | 50 |
| phenyl | .12 | .25 | 1 |
| o-tolyl | 20 | .35 | 4 |
| p-tolyl | 1.2 | .25 | 45 |
| o-allylphenyl | .5 | 1 | >100 |
| o-trifluoromethylphenyl | 6.0 | 2.5 | >100 |
| o-anisyl | .06 | .3 | .6 |
| m-anisyl | .15 | 4.5 | .45 |
| p-anisyl | .16 | .01 | — |
| o-fluorophenyl | .1 | 3.5 | 10 |
| m-fluorophenyl | .05 | .8 | 4 |
| p-fluorophenyl | 2 | 1 | .25 |
| p-chlorophenyl | .8 | .2 | >100 |
| 2,4-difluoro- | >100 | 4.5 | >100 |

TABLE 2-continued $$R-O-CH(C_6H_5)-CH_2-CH_2-NH-CH_3$$

| | Concentration in mcg./ml. that blocks 50% of amine uptake | | |
|---|---|---|---|
| R | Norepinephrine 0.48 μM | Serotonin 0.1 μM | Dopamine 0.2 μM |
| phenyl | | | |

One demonstration of the in vivo effect of the compounds of this invention in blocking serotonin uptake was made indirectly by the following experiment, based on a previous experiment of Meek et al. *Biochem. Pharmacol.*, 20, 707 (1971) who found that inhibitors of serotonin uptake prevent the depletion of brain serotonin caused by the injection of 4-chloromethamphetamine. In our procedure, an amount of 4-chloroamphetamine known to deplete the brain serotonin level about 50 percent was injected into rats. Following this injection, the protecting drug was injected at a dose of 15 mg./kg. of rat-weight intraperitoneally and determinations of brain serotonin levels were carried out 4 hours later. In Table 3 which follows, column 1 gives the name of the drug employed, the column 2, the brain serotonin levels in mcg./g. of brain tissue. Chloroimipramine and N-desmethylimipramine were employed as controls since Meek et al. (loc. cit.) had previously shown that these drugs were capable of preventing the depletion of brain serotonin by 4-chloromethamphetamine.

TABLE 3

| Name of drug | Brain serotonin level in mcg./g |
|---|---|
| none | 0.33 ± .02 |
| N—methyl 3-(p-trifluoromethylphenoxy)-3-phenylpropylamine oxalate | 0.69 ± .02 |
| chloroimipramine | 0.45 ± .03 |
| desmethylimipramine | 0.44 ± .03 |
| saline control | 0.70 ± .02 |

As can be seen from Table 3, N-methyl 3-(p-trifluoromethylphenoxy)-3-phenylpropylamine as the oxalate salt prevented the depletion of serotonin caused by the injection of 4-chloroamphetamine; and brain levels of serotonin were indistinguishable from those of the control rats to whom no drugs were given. The corresponding tertiary and primary amine derivatives, N,N-dimethyl 3-(p-trifluoromethylphenoxy)-3-phenylpropylamine oxalate and 3-(p-trifluoromethylphenoxy)-3-phenylpropylamine oxalate gave similar results. The secondary amine also prevented the depletion of serotonin in the brain occasioned by the administration of α-ethyl-4-methyl-m-tyramine but not the depletion of norepinephrine.

The tricyclic antidepressant drugs presently being marketed inhibit the uptake of monoamines by brain neurons, most of them being more effective in inhibiting the uptake of norephinephrine. Many of the compounds of this invention behave similarly in that they block norephinephrine uptake more effectively than they do serotonin uptake. Exceptions are the aforementioned p-trifluoromethyl derivatives, the dimethylamino, monomethylamino and unsubstituted amine derivatives being far more effective in inhibiting serotonin uptake than in inhibiting norepinephrine uptake. Thus, although the compounds of this invention clearly have potential as antidepressant compounds, it is apparent that N-methyl 3-(p-trifluoromethylphenyloxy)-3-phenylpropylamine and its tertiary and primary amine analogs will have a different type of anti-depressant action from the presently marketed drugs. The compounds may also find use in the treatment of schizophrenia according to the hypothesis of Wyatt et. al. *Science*, 177, 1124 (1972) who were able to produce mild to moderate improvement in 6 of 7 chronic undifferentiated schizophrenic patients by the oral administration of 1-5-hydroxytryptophane, a serotonin precursor.

In addition to their usefulness as psychotropic agents, the above compounds may also find use in treating disorders of sleep, sexual performance, appetite, muscular function, and pituitary function. All of these physiologic functions have been shown to be subject to influence by brain serotoninergic neural systems.

The ability of the compounds of this invention to alter the uptake of monoamines at brain neurons in mammals makes them effective in the treatment of consumptive disorders, eg. appetite. By blocking monoamine uptake, the compounds effectively diminish the craving sensation that often is experienced by a mammal, either as a direct result of a biological need or from use of a habit forming substance such as alcohol or tobacco. The compounds accordingly can be employed in the treatment of disorders of appetite (anti-obesity, carbohydrate craving, etc.) and other consumptions such as alcoholism, drug addiction and smoking.

Several of the invention compounds have been evaluated as anti-consumptive agents. The compound (−)-N-methyl-3-(o-methylphenoxy)-3-phenylpropylamine is now referred to generically as tomoxetine. Tomoxetine hydrochloride has now been evaluated clinically and shown to be an effective anti-depressant agent as well as an antiobesity agent.

The invention compound (+)-N-methyl-3-(p-trifluoromethylphenoxy)-3-phenylpropylamine is now generically known as fluoxetine. Fluoxetine, as the hydrochloride salt, has been clinically evaluated for its ability to treat disorders of appetite. In one study, patients were divided into overweight, normal, and underweight, using the weight ranges set forth in tables published in 1983 by Metropolitan Life Insurance Company. Patients with weights twenty percent below the midpoint of a range were defined as underweight, and those with weights twenty percent above the midpoint of a range were defined as overweight. The absolute weight loss in the fluoxetine-treated group, as compared to controls, was largest in the overweight group. Significant weight loss was also seen in the normal group, but not in those who were underweight during the study period. The results of the study are presented in the following Table 3A.

TABLE 3A

| | Overweight | | Normal | | Underweight | |
|---|---|---|---|---|---|---|
| | Fluoxetine (n = 52) | Placebo (n = 56) | Fluoxetine (n = 190) | Placebo (n = 194) | Fluoxetine (n = 16) | Placebo (n = 17) |
| baseline (lbs) | 198.8 | 202.5 | 145.0 | 147.5 | 112.1 | 124.6 |
| Endpoint (lbs) | 195.8 | 202.1 | 142.7 | 147.4 | 110.2 | 123.4 |

TABLE 3A-continued

|  | Overweight | | Normal | | Underweight | |
|---|---|---|---|---|---|---|
|  | Fluoxetine (n = 52) | Placebo (n = 56) | Fluoxetine (n = 190) | Placebo (n = 194) | Fluoxetine (n = 16) | Placebo (n = 17) |
| (up to 6 weeks) | | | | | | |
| Difference (lbs) | −3.0 | −0.3 | −2.3 | −0.1 | −1.9 | −1.1 |
| Significance | p = 0.002 | | p < 0.001 | | p > 0.5 | |

In another antiobesity study, patients were selected who were between 20 and 100 percent above the mean of the range of ideal body weight, again using the 1983 Metropolitan Life Insurance Company height, weight, and frame tables. Twenty-four fluoxetine-treated patients lost a mean of 4.29 pounds over a six-week period, while placebo controls (25) lost a mean of 1.44 pounds. The net weight loss of the fluoxetine versus the placebo group was 2.85 pounds, significant at p=0.055. These results are shown in Table 3B.

TABLE 3B

| Treatment Group | mean weight loss (lbs) Baseline-Endpoint | p-value |
|---|---|---|
| Fluoxetine (n = 24) | 4.29 | 0.001 |
| Placebo (n = 25) | 1.44 | 0.082 |
| Difference | 2.85 | 0.055 |

In another aspect of their action as psychotropic drugs, specifically as antidepressants, the compounds of this invention show activity in antagonizing hypothermia induced by the injection of apomorphine and also in antagonizing the central effects of tremorine and oxotremorine, including hypothermia. In addition, the compounds are effective in reversing reserpine hypothermia, but are less effective in preventing reserpine hypothermia. In this regard, the monomethylamines of this invention above are in general more active in antagonizing or reversing hypothermia than are their dimethylamino analogs.

The apomorphine hypothermia antagonism test is carried out as follows: mice are injected with a dose of apomorphine known to reduce body temperature approximately 4° C. The compound under test is injected ½ hour before the injection of the apomorphine and the temperatures measured ½ hour after injection. The degree of antagonism is expressed as a percent reduction (as compared with controls) of the temperature decrease produced by the injection of the apomorphine. The reserpine hypothermia reversal test is carried out as follows: groups of mice are injected with reserpine and 16.5 hours later are injected intraperitoneally with graded doses of the drug, a different dose level being given to each group of mice. Temperatures are measured at 1 hour after injection of the drug under test and again the effectiveness of the drug is expressed as a percentage decrease in the hypothermia induced by the injection of reserpine as compared with the control group. In the tables which follow, Table 4 gives the results in the apomorphine antagonism and reserpine reversal hypothermia tests for the secondary amines of this invention. In the table, the first column gives the substituent attached to the oxygen atom at the 3 position of the propylamine chain; columns 2 to 4 the percent antagonism against apomorphine hypothermia at dose levels of 0.3, 1 and 3 mg./kg. and columns 5–7 the percent reversal of reserpine hypothermia at the same dose levels. Table 5 gives similar information for the dimethylamino compounds of this invention.

TABLE 4

R—O—CH—CH$_2$—CH$_2$—NH—CH$_3$
|
C$_6$H$_5$

| | Percent Antagonism | | | | | |
|---|---|---|---|---|---|---|
| | Apomorphine Pre-30 min. | | | Reserpine Post-60 min. | | |
| | Dosage in mg./kg. | | | | | |
| | .3 | 1 | 3 | .3 | 1 | 3 |
| phenyl | 16 | 36 | 86 | 7 | 27 | 36 |
| o-tolyl | 20 | 37 | 92 | 14 | 18 | 24 |
| o-allylphenyl | 19 | 29 | 120 | — | 11 | 29 |
| o-trifluoromethylphenyl | — | 13 | 28 | — | 9 | 8 |
| p-trifluoromethylphenyl | — | 11 | 25 | — | — | 10 |
| p-tolyl | — | — | 33 | — | — | 17 |
| 2,4-difluorophenyl | 20 | 53 | 64 | 13 | 17 | 27 |
| o-anisyl | 47 | 101 | 121 | 17 | 55 | 58 |
| m-anisyl | 15 | 15 | 71 | 8 | 21 | 21 |
| p-anisyl | 0 | 31 | 45 | 12 | 23 | 20 |
| o-fluorophenyl | 13 | 57 | 87 | 10 | 8 | 34 |
| m-fluorophenyl | 28 | 53 | 89 | 13 | 12 | 19 |
| p-fluorophenyl | 7 | 19 | 66 | 7 | 39 | 32 |
| m-chlorophenyl | 11 | 58 | 136 | — | 12 | 38 |
| p-chlorophenyl | 32 | 29 | 37 | — | 9 | 23 |

TABLE 5

$$R-O-CH-CH_2-CH_2-N\begin{matrix}CH_3\\\\CH_3\end{matrix}$$
|
C$_6$H$_5$

| | Percent Antagonism | | | | | | |
|---|---|---|---|---|---|---|---|
| | Apomorphine Pre-30 min. | | | | Reserpine Post-60 min. | | |
| | Dosage in mg./kg. | | | | | | |
| | .3 | 1 | 3 | 10 | .3 | 1 | 3 | 10 |
| phenyl | | | 3 | 54 | | | 20 | 49 |
| o-tolyl | | | 11 | 94 | | | 26 | 31 |
| o-ethylphenyl | | | 20 | 74 | | 17 | 13 | 35 |
| o-isopropylphenyl | 3 | 17 | 39 | 65 | 12 | 20 | 28 | 35 |
| o-allylphenyl | | | 11 | 67 | | | | 27 |
| o-trifluoromethylphenyl | | 21 | 32 | 55 | | | | 10 |
| p-trifluoromethylphenyl | | | | 24 | | | | 20 |
| 2,4-difluorophenyl | | 26 | 55 | 98 | 23 | 11 | 12 | 30 |
| o-anisyl | | 11 | 30 | 61 | | 17 | 16 | 48 |
| m-anisyl | −12 | −7 | −5 | | −1 | 6 | 5 | |
| p-anisyl | | | 25 | | | | | 67 |
| o-phenetyl | | | 13 | 76 | | | 16 | 40 |
| o-fluorophenyl | −10 | 11 | 31 | | −1 | 26 | 40 | |
| m-fluorophenyl | | | 24 | 41 | | | 10 | 25 |
| p-fluorophenyl | 26 | 63 | 116 | 14 | 10 | 24 | 49 | |
| o-chlorophenyl | −10 | −17 | 57 | | 3 | 4 | 25 | |
| m-chlorophenyl | 0 | 13 | 66 | | 9 | 10 | 21 | |
| p-chlorophenyl | 7 | 43 | 85 | | 5 | 11 | 29 | |
| o-bromophenyl | 19 | 40 | 47 | | | 18 | 30 | |
| α-naphthyl | −17 | −10 | −7 | | 15 | 4 | 15 | |

Reversal of reserpine hypothermia and antagonism of apomorphine hypothermia are pharmacologic tests in which a number of marketed antidepressants drugs: in particular, imipramine, amitriptyline, nortriptyline and desmethylimipramine, are active. One of the compounds of this invention, N-methyl-3-(o-methoxyphenoxy)-3-phenylpropylamine has been found to be an apomorphine and reserpine hypothermia antagonist or reversant having an activity of the same order of magnitude as the aforementioned marketed antidepressant drugs. This compound, when its effect is measured 60 minutes after injection of the apomorphine, at a 10 mg./kg. dose gives 100 percent reduction of hypothermia, as do imipramine and amitriptyline. Similarly the same drug is extremely effective in reversing the effects of reserpine hypothermia and compares favorable in this regard with the same four marketed antidepressant compounds, giving a similar degree of reversal of hypothermia measured at 60 and 120 minutes.

In manifesting their psychotropic action, the compounds of this invention also affect the behavior of animals trained in a variety of operant behavior schedules. Again, the activity of compounds of this invention in this type of test parallels that of known antidepressant drugs, particularly desmethylimipramine. For example, N-methyl 3-(o-methoxyphenoxy)-3-propylamine increased response rates of pigeons in a fixed-ratio, fixed interval schedule and there was a persistence of this effect lasting for more than 24 hours. A similar effect was obtained with desmethylimipramine although it is possible that the persistence encountered was the result of training under the influence of the drug. In Sidman avoidance, using squirrel monkeys, the response of the monkeys increased at a dose level or 5 mg./kg. with N-methyl 3-(o-methoxyphenoxy)-3-phenylpropylamine. Similarly, in monkeys on a multiple fixed-ratio fixed-interval schedule, responses were reduced at dose levels of 2.5 or 5 mg./kg. of the drug. With pigeons trained under an adjusting ratio schedule, the drugs of this invention affect behavior in the same way as does the marketed antidepressant, desmethylimipramine (DMI). In this test, drugs with this type of activity do not markedly affect the response rate but pausing is decreased, as reflected in an increased response per reinforcement. N-methyl 3-(o-methoxyphenoxy)-3-phenylpropylamine, however, gave a significant percent increase in the ratio of responses to reinforcements at dose levels one-fourth of that required by DMI to produce a similar increase. The above results are consistent with anti-depressant action.

Finally, the compounds of this invention do not have significant antiserotonin, antihistaminic and anticholinergic effects when tested in isolated muscle strips using routine laboratory procedures. Again, there was a difference between N-methyl 3-(o-methoxyphenoxy)-3-phenylpropylamine as compared with desmethylimipramine, which latter compound was 150 times more potent as an antihistaminic and anticholinergic agent and three times more potent as an antiserotonin agent. In anesthetized cats, intravenous injection of amitriptyline and other marketed tricyclic antidepressants causes a widening of the QRS complex of the electrocardiogram, indicating a delay in intra-ventricular conduction. 3-(o-Methoxyphenoxy)-3-phenylpropylamine affects the electrocardiogram similarly, but at far higher doses than are found with the aforementioned marketed antidepressants.

In testing humans suffering from various psychoses having a depressive component, the compounds of this invention can be given orally or parenterally. In either instance, it is preferred to use an acid addition salt of the compound formed with a pharmaceutically-acceptable non-toxic acid. For purposes or oral administration, the salt can be mixed with standard pharmaceutical excipients and placed in telescoping gelatin capsules. Similarly, the compound can be mixed with starch, binders, etc. and formulated into tablets, which tablets may be scored for ease of divided dosage administration. For parenteral administration, a water soluble salt of the compound of this invention, which salt is pharmaceutically-acceptable, is dissolved in an isotonic solution and administered intramuscularly, intravenously or subcutaneously. For chronic administration, the oral pharmaceutical forms are naturally preferred. The dose level should vary from 1 to 50 mg./dose given from 1 to 4 times a day with a total daily dosage of 1 to 200 mg./day/human.

We claim:

1. A method of treating animals suffering from an appetite disorder comprising administering to said animal an effective amount of a compound of the formula

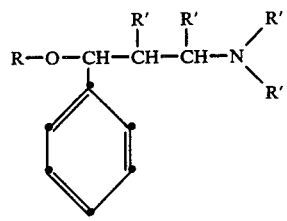

wherein each R' is independently hydrogen or methyl; wherein R is naphthyl or

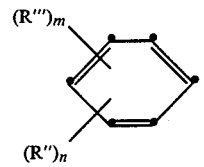

wherein R" and R''' are halo, trifluoromethyl, $C_1$–$C_4$ alkyl, $C_1$–$C_3$ alkyloxy or $C_3$–$C_4$ alkenyl; and
wherein n and m are 0, 1 or 2; and acid addition salts thereof formed with pharmaceutically-acceptable acids.

2. A method according to claim 1 employing N-methyl-3-(p-trifluoromethylphenoxy)-3-phenylpropylamine or a pharmaceutically-acceptable acid addition salt thereof.

3. The method of claim 2 employing N-methyl-3-(p-trifluoromethylphenoxy)-3-phenylpropylamine hydrochloride.

4. A method of blocking the uptake of monoamines by brain neurons in animals comprising administering to said animal a monoamine blocking amount of a compound of the formula

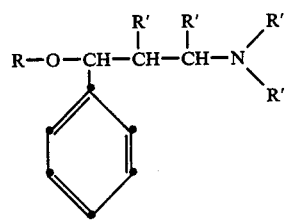

wherein each R' is independently hydrogen or methyl; wherein R is naphthyl or

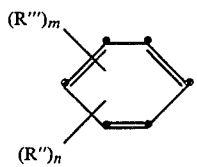

wherein R″ and R‴ are halo, trifluoromethyl, $C_1$–$C_4$ alkyl, $C_1$–$C_3$ alkyloxy or $C_3$–$C_4$ alkenyl; and wherein n and m are 0, 1 or 2; and acid addition salts thereof formed with pharmaceutically-acceptable acids.

5. A method according to claim 4 wherein the monoamine to be blocked is serotonin.

6. A method according to claim 5 employing N-methyl-3-(p-trifluoromethylphenoxy)-3-phenylpropylamine or a pharmaceutically-acceptable acid addition salt thereof.

7. The method of claim 6 employing N-methyl-3-(p-trifluoromethylphenoxy)-3-phenylpropylamine hydrochloride.

8. The method of claim 5 employing N-methyl-3-(o-methylphenoxy)-3-phenylpropylamine or a pharmaceutically-acceptable acid addition salt thereof.

9. The method of claim 5 employing N-methyl-3-(o-methylphenoxy)-3-phenylpropylamine hydrochloride.

* * * * *